United States Patent [19]

Clarkson

[11] Patent Number: 4,666,710

[45] Date of Patent: May 19, 1987

[54] ANTI-PERSPIRANT COMPOSITIONS

[75] Inventor: Roy J. Clarkson, Maidenhead, England

[73] Assignee: Beecham Group P.L.C., England

[21] Appl. No.: 121,174

[22] Filed: Feb. 13, 1980

[30] Foreign Application Priority Data

Feb. 22, 1979 [GB] United Kingdom ............... 7906281

[51] Int. Cl.$^4$ ........................... A61K 7/34; A61K 7/38
[52] U.S. Cl. .......................................... 424/66; 424/68
[58] Field of Search ............................. 424/66, 67, 68

[56] References Cited

U.S. PATENT DOCUMENTS

| | | | |
|---|---|---|---|
| 4,053,581 | 10/1977 | Pader et al. | 424/68 |
| 4,152,416 | 5/1979 | Spitzer et al. | 424/67 |
| 4,174,386 | 11/1979 | Spitzer et al. | 424/67 |

FOREIGN PATENT DOCUMENTS

| | | |
|---|---|---|
| 480379 | 2/1938 | United Kingdom . |
| 1267959 | 3/1972 | United Kingdom . |
| 1319437 | 6/1973 | United Kingdom . |

OTHER PUBLICATIONS

Ash et al., A Formulary of Cosmetic Preparations, 1977, pp. 7, 8, 9, 10 to 14, & 20 to 24.

*Primary Examiner*—Dale R. Ore
*Attorney, Agent, or Firm*—Jacobs & Jacobs

[57] ABSTRACT

An anti-perspirant composition includes 30% by weight of an anti-perspirant agent, aluminium chlorhydrate, 68.5% by weight of ethanol and 1.5% by weight of a long chain fatty acid, myristic acid.

The presence of the fatty acid counteracts the reduction in efficacy caused by the high concentration of ethanol.

7 Claims, No Drawings

ANTI-PERSPIRANT COMPOSITIONS

This invention relates to anti-perspirant compositions.

A desirable property of anti-perspirant compositions is that they should dry quickly after application to the skin. The inclusion of a volatile solvent in the composition may often achieve this effect, the solvent evaporating quickly after application to leave a dry deposit of the active anti-perspirant material on the skin. Ethanol has often been used for this purpose, since it is readily available and relatively non-toxic. However, the use of high concentrations of ethanol can seriously reduce the efficacy of certain anti-perspirant compositions. This is particularly marked in the case of compositions containing an astringent anti-perspirant such as aluminium chlorhydrate.

It is an object of the present invention to provide aqueous anti-perspirant compositions which contain relatively high levels of ethanol to promote quick drying after application to the skin, and which have good levels of anti-perspirant efficacy.

We have discovered that the reduction in efficacy caused by the presence of high concentrations of ethanol may be counteracted by the addition of certain fatty acids.

The addition of, inter alia, fatty acids to anti-perspirant compositions containing "Rehydrol" (a complex of aluminium chlorhydrate and propylene glycol) has been suggested. This is to counteract gelling of the compositions, which can occur with "Rehydrol". Gelling is not normally a problem with aqueous aluminium chlorhydrate compositions, so there has been no suggestion that the addition of fatty acids to aqueous aluminium chlorhydrate compositions would have any beneficial effects.

Accordingly, this invention provides an aqueous antiperspirant composition comprising from 2 to 30% by weight of an astringent aluminium or zirconium salt as anti-perspirant agent, from 30 to 80% by weight of ethanol, and from 0.1 to 6% by weight of one or more $C_{14-18}$ fatty acids.

Anti-perspirant agents suitable for use with the composition include aluminium basic chloride, bromide or iodide, zirconyl hydroxychloride, and astringent aluminium/zirconium complexes such as aluminium zirconium chlorhydrates.

When used herein, "aluminium basic chloride" means a compound having the approximate empirical formula $Al_2(OH)_{(6-x)}Cl_x$, where x is a number from 1 to 5. The corresponding bromide and iodide have analogous formulae.

Preferably, the compositions of the invention contain from 0.5 to 4%, or more preferably 1.0 to 3% by weight of one or more $C_{14-18}$ fatty acids.

Suitable fatty acids include myristic, palmitic, stearic and iso-stearic acids, and mixtures thereof. The most highly preferred fatty acids are myristic and palmitic acids.

The compositions of the invention will normally contain from 5 to 20% by weight of anti-perspirant agent.

The preferred anti-perspirant agent for use in the compositions of the invention is an aluminium basic chloride wherein the atomic ratio of aluminium to chloride is from 1.9:1 to 2.1:1. This material is generally known as aluminium chlorhydrate.

The compositions may contain further ingredients if desired, such as perfume, which will be present at conventional levels, such as 0.5 to 1% by weight.

The compositions of the invention are more effective anti-perspirants than analogous compositions without fatty acids.

The compositions will generally be adapted for application from a roll-ball or spray applicator. Metal containers, such as those used for aerosol compositions, are generally unsuitable for use with the present compositions since they may be subject to corrosion. Glass or plastic containers are therefore preferred.

Compositions adapted for application from a roll-ball applicator will generally be thickened, for example, by the addition of conventional thickening agents, such as hydroxypropyl cellulose, or other thickening agents well known to those skilled in the art of formulating cosmetic compositions. When hydroxypropyl cellulose is used as thickening agent, it will generally be present in the composition in an amount from 0.1 to 2% by weight, more usually 0.1 to 1% or 0.3 to 0.8% by weight.

The compositions may also be adapted for application from spray applicators, such as pump-sprays or squeeze-bottles.

The compositions of the invention may be prepared as follows:

Dissolve the fatty acid(s) in the alcohol with stirring, and then add the thickener (if required) and stir until dissolved. Finally, add an aqueous solution of the anti-perspirant agent and stir thoroughly. Perfume may be added to the composition before adding the anti-perspirant agent.

The following Examples illustrate the invention:

EXAMPLE 1

|  | % by weight |
| --- | --- |
| Myristic acid | 1.5 |
| Denatured ethanol | 68.5 |
| Aluminium chlorhydrate (50% aqueous solution) | 30.0 |

The myristic acid was dissolved in the ethanol with stirring, and then the aluminium chlorhydrate solution was added, and the mixture was stirred thoroughly.

In the axilla screening test described in *J. Soc. Cosmet. Chem.* 29, 413–422 (1978), this composition produced a 43% sweat reduction compared with a 32% reduction for a corresponding composition containing no myristic acid and with 70% ethanol. (Significantly different at 0.02% level in Wilcoxon Matched Pairs Test).

EXAMPLE 2

|  | % by weight |
| --- | --- |
| Myristic Acid | 1.5 |
| Denatured ethanol | 67.84 |
| Klucel H* | 0.66 |
| Aluminium chlorhydrate (50% aqueous solution) | 30.00 |

*Klucel H is hydroxypropyl cellulose (Hercules Powder Co.).

The myristic acid was dissolved with stirring in the ethanol, followed by Klucel H, and then the aluminium chlorhydrate solution was added. The mixture was thoroughly stirred, to produce a composition suitable for application to the skin from a roll-ball applicator.

EXAMPLE 3

|  | % by weight |
|---|---|
| Fatty Acid | 1.5 |
| Aluminium Chlorhydrate | 30.0 |
| (50% aqueous solution) |  |
| Denatured ethanol | 68.5 |

Using the method described in Example 1, three compositions having the above constitution were prepared. The fatty acids used were myristic, palmitic and isostearic acids.

These compositions and a corresponding composition containing no fatty acid were tested on 20 subjects using the back screening method descrived in *J. Soc. Cosmet. Chem.* 29, 413–422 (1978).

The results are shown below.

| Fatty Acid | Mean % Sweat Reduction |
|---|---|
| — | 34 |
| Myristic | 54 |
| Palmitic | 54 |
| Isostearic | 39 |

EXAMPLE 4

A composition analogous to those in Examples 1 and 3 but having Crosterene S4310, a mixture of fatty acids, $C_{16}$ and $C_{18}$ acids predominating (Croda Chemicals Ltd.) was prepared and tested on 8 subjects using the back screening test, together with a corresponding composition containing no fatty acid. The compositions produced mean sweat reductions of 46% and 17%, respectively.

I claim:

1. An aqueous anti-perspirant composition, consisting essentially of from 2 to 30% by weight of an astringent aluminium or zirconium salt as anti-perspirant agent, from 30 to 80% by weight of ethanol, from 0.16 to 6% by weight of one or more $C_{14\text{-}18}$ fatty acids, and water.

2. A composition according to claim 1, wherein the anti-perspirant agent comprises aluminium basic chloride, bromide, or iodide, zirconyl hydroxychloride, or an aluminium zirconium chlorohydrate.

3. A composition according to claim 1, wherein from 1.0 to 3% by weight of one or more $C_{14\text{-}18}$ fatty acids is present.

4. A composition according to claim 1, wherein the fatty acid is myristic, palmitic, stearic, or iso-stearic acid, or a mixture of any thereof.

5. A composition according to claim 1, wherein from 5 20% by weight of said anti-perspirant agent is present.

6. An aqueous anti-perspirant composition, consisting essentially of from 2 to 30% by weight of an astringent aluminium or zirconium salt as anti-perspirant agent, from 30 to 80% by weight of ethanol, from 0.16 to 6% by weight of one or more $C_{14\text{-}18}$ fatty acids, and water and a thickener.

7. An aqueous anti-perspirant composition consisting essentially of from 2 to 30% by weight of an astringent aluminium or zirconium salt as anti-perspirant agent, from 30 to 80% by weight of ethanol, from 0.16 to 6% by weight of one or more $C_{14\text{-}18}$ fatty acids, and water and a perfume.

* * * * *